US00PP23531P3

(12) United States Plant Patent
Cain

(10) Patent No.: US PP23,531 P3
(45) Date of Patent: Apr. 16, 2013

(54) GRAPEVINE 'IFG SIX'

(50) Latin Name: *Vitis vinifera*
Varietal Denomination: IFG Six

(75) Inventor: David Cain, Bakersfield, CA (US)

(73) Assignee: International Fruit Genetics LLC, Bakersfield, CA (US)

( * ) Notice: Subject to any disclaimer, the term of this patent is extended or adjusted under 35 U.S.C. 154(b) by 0 days.

(21) Appl. No.: 13/134,947

(22) Filed: Jun. 22, 2011

(65) Prior Publication Data

US 2012/0331596 P1 Dec. 27, 2012

(51) Int. Cl.
*A01H 5/00* (2006.01)

(52) U.S. Cl. ..... Plt./205

(58) Field of Classification Search ..... Plt./205
See application file for complete search history.

*Primary Examiner* — Annette Para

(57) ABSTRACT

This invention is a new and distinct grapevine variety denominated 'IFG Six'. The new grapevine is characterized by producing naturally large, extremely elongated, narrow diameter, crisp, seedless black berries having a distinct dimple on the distal end. The fruit ripen and are commercially harvestable from late August to mid-September. Berries color to full black and store well.

1 Drawing Sheet

Latin name of the genus and species claimed: *Vitis vinifera*. Variety denomination: 'IFG Six'.

BACKGROUND OF THE INVENTION

The new and distinct grapevine described and claimed herein originated from a hand pollination of the Beita Mouni (non-patented) variety and an unnamed USDA selection designated 'C22-121' performed in May 2004. The resulting plants were planted into the field in April 2005. The present variety of grapevine was selected as a single plant in July 2006 and was first asexually propagated by hardwood cuttings in December 2006, near Delano, Kern County, Calif. The resulting propagules were planted during April 2007 near Delano, Kern County Calif.

BRIEF SUMMARY OF THE INVENTION

The new grapevine 'IFG Six' is characterized by producing large, extremely elongated cylindrical seedless black fruit with a characteristic dimpled tip. The shape, which to the author's knowledge is unique among seedless table grape varieties, provides consumers with a distinct visual signal to identify the new variety. The new variety is further characterized by producing large berries that do not require any gibberellic acid application or trunk girdling to attain commercially acceptable berry size. Berries are completely black, crisp in texture and of high eating quality. Vines of 'IFG Six' are moderately productive. The fruit ripen in mid to late August and are moderately prone to sunburn damage. Fruit store well and are suitable for international commerce and long-term cold storage.

'IFG Six' differs from its maternal parent by producing elongated black seedless berries as opposed to seeded white fruits of the 'Beita Mouni'. It differs from its pollen parent by producing much larger more crisp seedless berries with a distinct dimpled end which the 'C22-121' lacks.

BRIEF DESCRIPTION OF THE FIGURE

The accompanying photographic illustration in FIG. 1 illustrates in full color 'IFG Six'. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Six' plants grown in the vicinity of Delano, Kern County, Calif. during 2009 and 2010, and is believed to apply to plants of the variety grown under similar conditions of soil and climate elsewhere:

VINE

General:

*Size*.—Large-Medium.
*Vigor*.—Vigorous.
*Density of foliage*.—Medium.
*Productivity*.—Moderately Productive.
*Root stock*.—Own root.
*Training method*.—Typically spur pruned leaving 2 bud spurs but may benefit from longer canes in some conditions.

Trunk:
- *Trunk diameter of 4-year-old vines at 30 cm above the soil line.*—6.1 cm.
- *Shape.*—Medium to Stocky.
- *Straps.*—Short — Split.
- *Surface texture.*—Medium rough.
- *Inner bark color.*—Can be any of the following colors; Brown; 165A and B, and 164A, and 177B.

SHOOTS

Young shoot:
- *Form of tip.*—Wide open.
- *Distribution of anthocyanin coloration of tip.*—Absent.
- *Intensity of anthocyanin coloration of tip.*—Absent.
- *Density of prostrate hairs of tip.*—Dense.
- *Density of erect hairs of tip.*—Absent.
- *Color.*—Can be any of the following colors; Green; 145A, and 146 A and B.

Woody shoot (mature canes):
- *Shape.*—Stocky — Medium Thick.
- *Internode length.*—Short; About 10.6 cm.
- *Width at node.*—About 0.8 cm.
- *Cross section.*—Circular.
- *Surface.*—Striate.
- *Main color.*—Can be any of the following colors; Yellowish brown; 166A and B and C and D, and 165A, and 164D, and 174A.
- *Density of erect hairs of nodes.*—Medium.
- *Density of erect hairs on internodes.*—Medium.
- *Growth of axillary shoots.*—Weak; Approximately 12.1 cm.

Flowering shoot:
- *Vigor during flowering.*—Strong.
- *Attitude during flowering on shoots not tied.*—Drooping.
- *Color.*—Dorsal side of internodes — Green with Red stripes.
- *Color.*—Ventral side of internodes — Green with Red stripes.
- *Color.*—Dorsal side of nodes — Green.
- *Color.*—Ventral side of nodes — Green with Red stripes.
- *Density of prostrate hairs of nodes.*—Sparse.
- *Density of erect hairs of nodes.*—Very sparse to Sparse.
- *Density of prostrate hairs on internode.*—Sparse.
- *Density of erect hairs on internode.*—None.
- *Anthocyanin coloration of buds.*—Absent.

Tendrils:
- *Distribution on the shoot (at full flowering).*—Discontinuous.
- *Length of tendril.*—Medium; About 21.7 cm.
- *Thickness.*—Medium to thick.
- *Color.*—Can be any of the following colors; Yellow-Green; N144A, and 144B and C.
- *Form.*—Bifurcated to Mostly trifurcated, occasionally bifurcated or quadfurcated.
- *Number of consecutive tendrils.*—2.

LEAVES

Young leaves:
- *Color of upper surface of first four distal unfolded leaves.*—Can be either of the following colors; Green; 144A, and 146A.
- *Average intensity of anthocyanin coloration of six distal leaves prior to flowering.*—Absent.
- *Density of prostrate hairs between veins (lower surface).*—Sparse.
- *Density of prostrate hairs on veins (lower surface).*—Medium.
- *Density of erect hairs between veins (lower surface).*—Absent.
- *Density of erect hairs on veins (lower surface).*—Sparse.

Mature leaves:
- *Average length.*—About 13.2 cm.
- *Average width.*—About 18.2 cm.
- *Mature leaf size.*—Small-Medium.
- *Shape of blade.*—Pentagonal.
- *Number of lobes.*—5.
- *Anthocyanin coloration of main veins on upper side of blade.*—Absent.
- *Mature leaf profile.*—Undulate.
- *Blistering surface of blade upper surface.*—Weak.
- *Leaf blade tip.*—In the plane of the leaf.
- *Undulation of margin.*—Medium.
- *Thickness.*—Medium.
- *Undulation of blade between main and lateral veins.*—Only near petiole.
- *Shape of teeth.*—Mixture of both sides straight and both sides convex.
- *Length of teeth.*—Short.
- *Ratio length/width of teeth.*—Small.
- *Shape of upper lateral sinuses.*—Lobes slightly overlapping.
- *Depth of upper lateral sinuses.*—Medium.
- *General shape petiole sinus.*—Lobes half overlapping.
- *Shape of base of upper leaf sinuses.*—U-shaped.
- *Shape of the base of the petiole sinus.*—V-shaped.
- *Tooth at petiole sinus.*—Absent.
- *Density of prostrate hairs between veins on lower surface of blade.*—Sparse.
- *Density if erect hairs between veins on lower surface of blade.*—Absent.
- *Density of prostrate hairs on main veins on lower surface of blade.*—Sparse-Medium.
- *Density of erect hairs on main veins on lower surface of blade.*—Sparse.
- *Density of prostrate hairs on main veins on upper surface of blade.*—Very sparse.
- *Density of erect hairs on main veins on upper surface of blade.*—None.
- *Autumn coloration of leaves.*—Leaves can be a single color or combination of colors, in a mottled pattern or on the edges of the leaves; Grey-Yellow; 162A and B, and Grey-Red; 181A and B, and 182A, and Grey-Purple; 187A and B, and 183C and D, and 187A.

Upper surface:
- *Color.*—Can be any of the following colors; Green; 147A, and 137A and B.
- *Anthocyanin coloration of main veins.*—Absent.
- *Surface appearance.*—Dull.
- *Blistering surface of blade.*—Weak to Medium.

Lower surface:
- *Color.*—Can be any of the following colors; Green; 137 B and C and D.
- *Anthocyanin coloration of main veins (lower surface).*—Absent.
- *Glossiness.*—Weak to Medium.
- *Surface texture.*—Rugose
- *Surface appearance.*—Semi-glossy to Dull. .

Petiole:

*Length*.—About 11.0 cm.

*Length of petiole compared to middle vein*.—Slightly shorter.

*Density of prostrate hairs on petiole*.—Sparse.

*Density of erect hairs on petiole*.—None.

Buds:

*Bud fruitfulness*.—Basal: Mostly fruitful.

*Position of first fruitful shoot on previous season cane*.—$1^{st}$ to $2^{nd}$ node.

*Time of bud burst*.—Very early; Feb. 18, 2010.

FLOWERS

General:

*Flower sex*.—Hermaphrodite.

*Length of first inflorescence*.—Medium; About 23.8 cm long by 12.9 cm wide.

*Position of first flowering and fruiting node*.—$4^{th}$-$5^{th}$ node (current season growth).

*Number of inflorescence per flowering shoot*.—1.1 to 2.

*Time of bloom*.—Medium as compared with similar varieties in the growing area of Delano, Calif.

*Date of full bloom*.—May 18, 2010.

FRUIT

General:

*Ripening period*.—Midseason; mid August to early September.

*Use*.—Fresh market.

*Keeping quality*.—Good.

*Resistance to*.—Insects: Average, typical of *Vitis vinifera* species. Diseases: Average, typical of *Vitis vinifera* species.

*Refractometer test*.—Solid-sugar: About 19.4 Brix.

*Brix/acid*.—About 51.1.

*Titratable acidity*.—About 0.38.

*Juice pH*.—About 3.88.

Cluster:

*Mature cluster length* (*peduncle excluded*).—About 29.0 cm.

*Mature cluster width*.—About 16.7 cm.

*Mature cluster weight*.—About 1079 g.

*Bunch density*.—Loose — usually requires no additional thinning.

*Number of berries*.—About 154.

*Form*.—Cylindrical.

Peduncle:

*Lignification of peduncle*.—Weak to Medium.

*Length of peduncle*.—Approximately 6.0 cm.

Berry:

*Uniformity of size*.—Uniform.

*Single berry weight*.—About 10.0 g.

*Shape*.—Cylindrical usually having a dimpled tip.

*Seeds*.—Absent.

*Cross section*.—Circular.

*Berry dimensions*.—Longitudinal axis: About 41 mm. Horizontal axis: About 18 mm.

*Berry firmness*.—Medium firm to crisp.

*Particular flavor*.—Neutral.

*Bloom* (*cuticular wax*).—Medium to heavy.

*Berry separation from pedicel*.—Medium strong.

*Skin color* (*without bloom*).—Blue-black; 202A.

Skin:

*Thickness*.—Medium.

*Texture*.—Medium tough.

*Reticulation*.—Absent.

*Tenacity*.—Tenacious to flesh.

What is claimed:

1. A new and distinct variety of grapevine as herein illustrated and described.

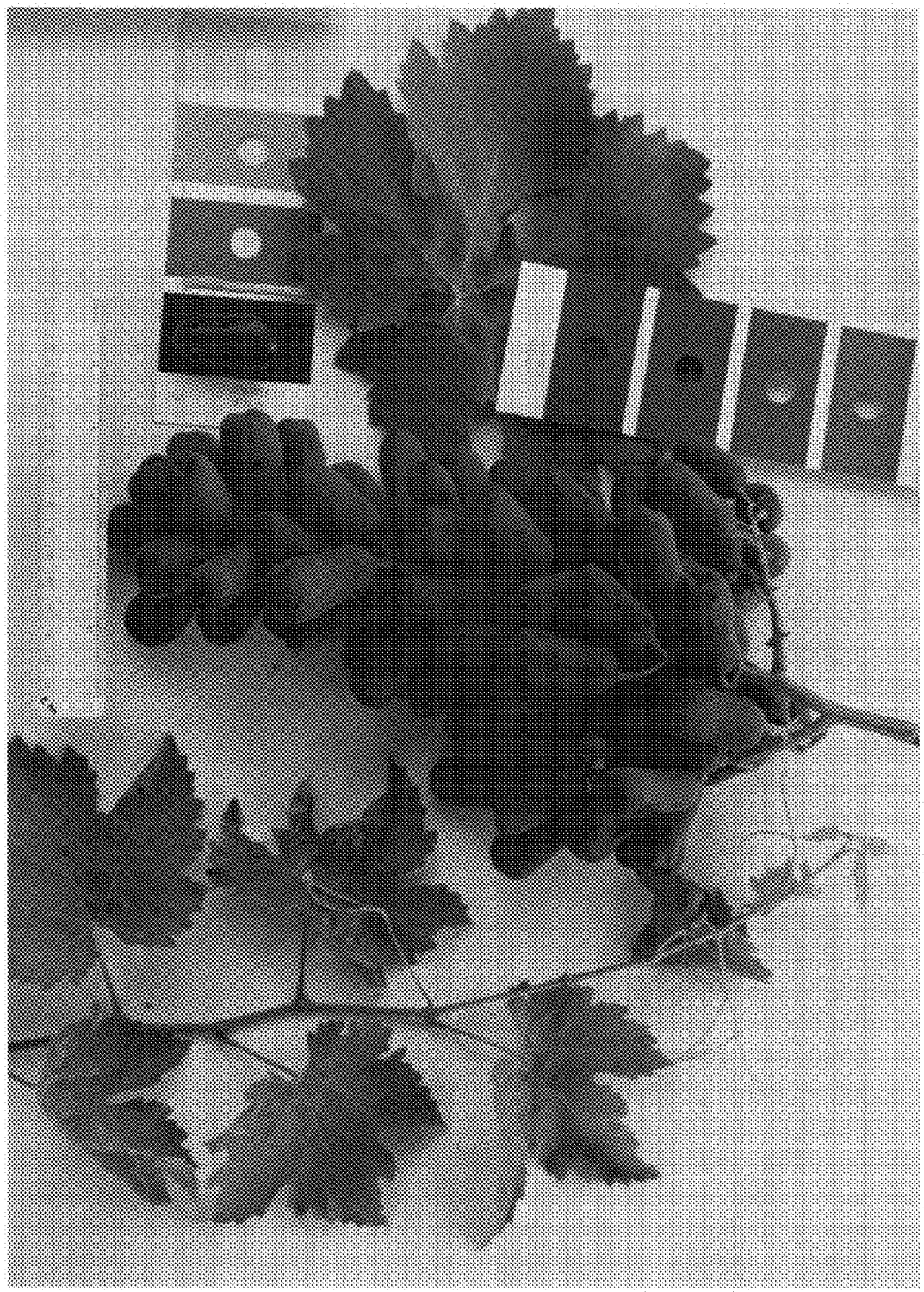

* * * * *